(12) United States Patent
Houston et al.

(10) Patent No.: US 7,114,524 B2
(45) Date of Patent: Oct. 3, 2006

(54) FLUID FLOW IN TUBING

(75) Inventors: Graeme J. Houston, Tayside (GB); Peter A. Stonebridge, Tayside (GB); John B. C. Dick, Tayside (GB)

(73) Assignee: Tayside Flow Technologies Limited, Tayside (GB)

( * ) Notice: Subject to any disclaimer, the term of this patent is extended or adjusted under 35 U.S.C. 154(b) by 290 days.

(21) Appl. No.: 10/450,805

(22) PCT Filed: Dec. 13, 2001

(86) PCT No.: PCT/GB01/05531

§ 371 (c)(1),
(2), (4) Date: Dec. 19, 2003

(87) PCT Pub. No.: WO02/47576

PCT Pub. Date: Jun. 20, 2002

(65) Prior Publication Data

US 2004/0079428 A1   Apr. 29, 2004

(30) Foreign Application Priority Data

Dec. 14, 2000   (GB) ................... 0030462.6

(51) Int. Cl.
*F15D 1/04*   (2006.01)

(52) U.S. Cl. .................. 138/37; 138/39; 138/177; 285/132.1; 285/131.1

(58) Field of Classification Search ............ 138/37, 138/39, 117, 116, 177, 178; 285/132.1, 131.1, 285/125.1
See application file for complete search history.

(56) References Cited

U.S. PATENT DOCUMENTS

| 1,329,285 | A | * | 1/1920 | Brownlee | 285/131.1 |
| 1,362,718 | A | * | 12/1920 | McNamara | 285/129.2 |
| 1,878,948 | A | * | 9/1932 | Luff | 285/129.2 |
| 2,065,789 | A | * | 12/1936 | Bolsinger | 237/59 |
| 2,505,303 | A | * | 4/1950 | Randa | 285/148.13 |
| 2,767,002 | A | * | 10/1956 | Schwinn | 403/169 |
| 3,670,773 | A | * | 6/1972 | Guerster | 138/155 |
| 3,734,140 | A | * | 5/1973 | Nakamura et al. | 138/177 |
| 3,945,052 | A | * | 3/1976 | Liebig | 623/1.5 |
| 4,047,252 | A | * | 9/1977 | Liebig et al. | 623/1.52 |
| 4,248,179 | A | * | 2/1981 | Bonner | 122/235.14 |
| 4,836,250 | A |   | 6/1989 | Krambrock | 137/625.47 |
| 4,892,539 | A | * | 1/1990 | Koch | 623/1.52 |
| 4,998,754 | A | * | 3/1991 | Matsumoto et al. | 285/125.1 |
| 5,054,818 | A | * | 10/1991 | Briet | 285/124.5 |
| 5,250,041 | A | * | 10/1993 | Folden et al. | 604/284 |
| 6,039,754 | A |   | 3/2000 | Caro | 623/1 |
| 6,390,142 | B1 | * | 5/2002 | Naito | 138/177 |

FOREIGN PATENT DOCUMENTS

| EP | 0 913 611 | 5/1999 |
| WO | WO 00/38591 | 7/2000 |

* cited by examiner

*Primary Examiner*—Patrick Brinson
(74) *Attorney, Agent, or Firm*—Pearne & Gordon LLP

(57) ABSTRACT

There is disclosed a method for configuring or reconfiguring branches in tubing in which the axes of at least two components of the branched structure are arranged askew.

13 Claims, 1 Drawing Sheet

FLUID FLOW IN TUBING

This invention relates to fluid flow in tubes, particularly, but by no means essentially, blood flow tubing and other tubing carrying fluids essential to life.

In WO 00/38591 is described tubing adapted to induce helical flow in such fashion as to eliminate or reduce turbulence and/or eliminate or reduce dead flow regions in the tubing. The tubing has internal helical grooving or ridging or other measures designed having regard to the dimensions of the tubing and the density, viscosity and velocity of the flow. Particular problems arise in connection with branched tubing, in which fluid flows from a main trunk into two or more branches, or, alternatively, flows from two or more branches into a main trunk. Certain blood carrying vessels as well as air passages in human or animal bodies experience such branching. When such branched tubing is repaired or replaced, as in vascular grafting, heart bypasses and so forth, it may be advantageous to reconfigure such tubing to improve fluid flow at such branch. One way of reconfiguring the tubing would be to introduce helical ridging or grooving in the manner taught in WO 00/38591, but this is not always possible.

In accordance with the present invention, there is provided a method of configuring or reconfiguring branches in tubing in which the axes of at least two components of the branched structure are neither intersecting nor parallel and in which at least one of the components of the branched structure itself has internal helical ridging and/or grooving adapted to reduce or eliminate turbulence and/or dead regions in flow through the tubing.

The axis of a circular section tube is, of course, well defined. More generally, the axis of a non-circular section tube is taken for present purposes to be the locus of the centres of gravity of adjacent lengthwise slices through the lumen of the tube. An axis may, then, not be a straight line, as the branch may be curved.

Typically, the internal helical ridging and/or grooving is adapted to cooperate with the skew arrangement of any components of the branched structure—if, for example, the skew arrangement is intended to produce a clockwise rotary component in the flow, viewed along the direction of flow, then the internal helical configuration of at least one component of the branched structure may also be arranged to produce a clockwise component To avoid the creation of incidental turbulence, it may be arranged that internal surfaces of the branched structure have no sharp edges.

Figure 1:
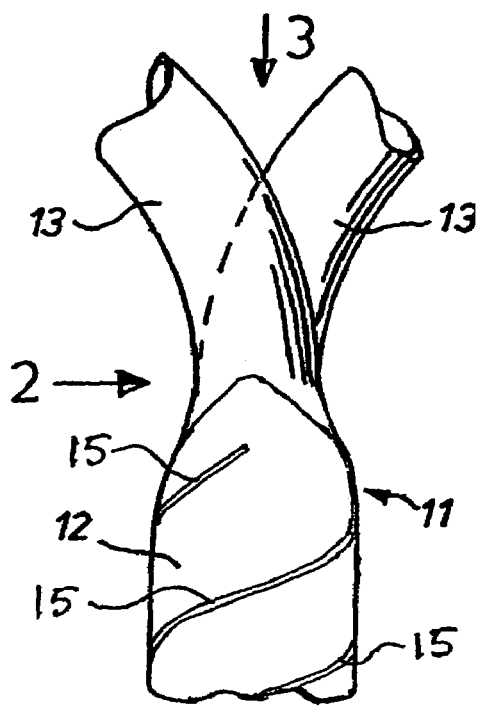
Figure 2:
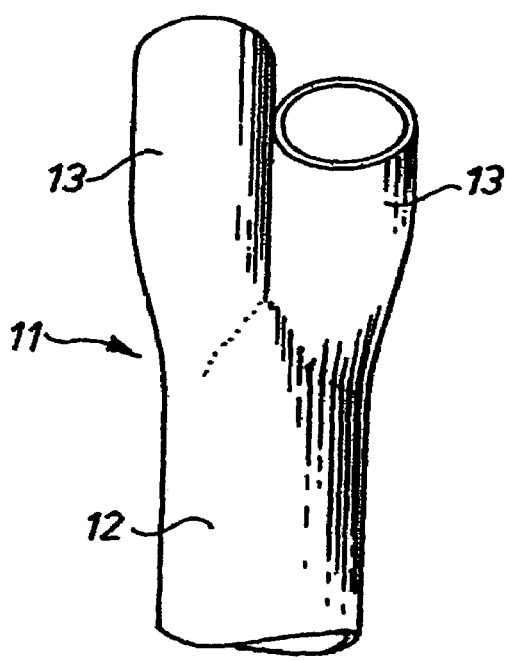
Figure 4:
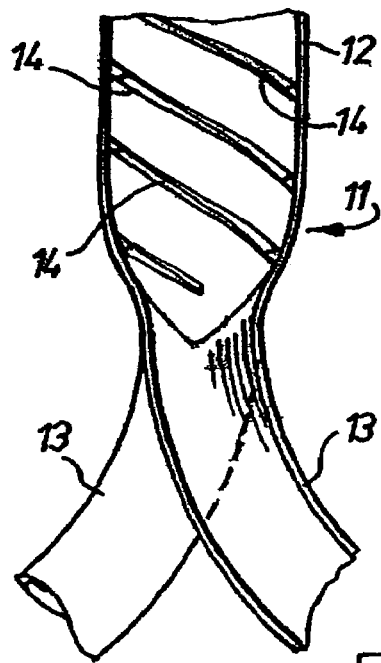
Figure 3:
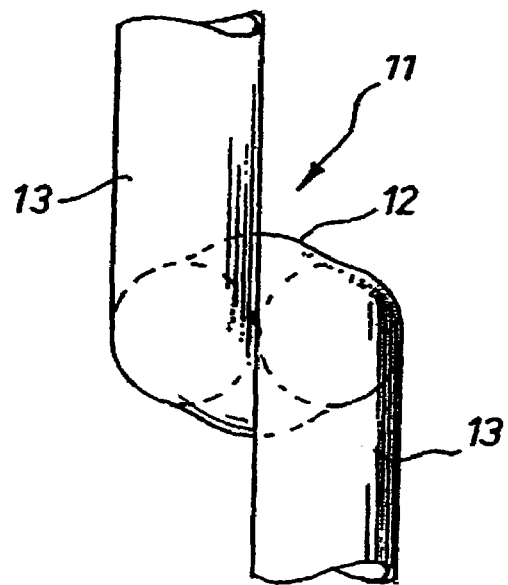

An example of a branched tubular configuration according to the invention will now be described with reference to the accompanying drawings, in which:

FIG. 1 is a lengthwise section through a first embodiment;
FIG. 2 is a non-sectional view on Arrow 2 of FIG. 1;
FIG. 3 is a non-sectional view on Arrow 3 of FIG. 1; and
FIG. 4 is a lengthwise section through a second embodiment.

The drawings illustrate methods for configuring branched tubular structures 11, each comprising a main trunk portion and two branches.

FIGS. 1 to 4 illustrate a structure in which fluid flow is into the main trunk 12 from two branches 13. The offset arrangement of the branches 13 causes rotational flow in the main trunk 12, as indicated by the flow arrows. In addition, the main trunk 12 includes internal helical ridging 15 that is adapted to cooperate with the skew arrangement of the branches 13 to aid production of rotary flow in the main trunk 12.

As the general idea is to reduce or eliminate turbulence and/or dead spaces, the branched structure will need to be configured as to the dimensions of the tubes, especially the relative flow capacities of the trunk 12 and branches 13, the viscosity and density of the fluid flowing in them and the flow velocities, to optimise the flow characteristics. It may be that this can all be worked out by computational fluid dynamics, or it may be dealt with on a trial and error basis in which a range of configurations is investigated.

FIG. 4 illustrates a branched structure in which the fluid is flowing from the main trunk 12 into the branches 13. Here, the flow is prepared in advance of the junction to have a rotational component in the correct sense by means of internal helical ridging and/or grooving 14 in the inner wall of the trunk 12.

Of course, structures of more complex geometry can be contemplated, for example a trunk dividing into three or more branches, a structure in which two or more branches flow into two or more further branches, and so forth, all of which can be dealt with by offsetting the branches as above described.

The invention may have particular relevance in relation to tubing in which body fluids flow, such for example as veins and arteries, for the avoidance or reduction of tendency to atherosclerosis and the formation of clots that can break away leading to strokes. The design of artificial vascular grafts and particularly patches for coronary bypass surgery may benefit from the teachings herein. A particularly important branched structure is the respiratory system, and, while surgical intervention may not bring about structures that were not already in place, at least the teachings herein may serve to avoid the creation of structures which create unwanted turbulence and/or dead spaces in the system.

The invention, however, will find many applications outside of the clinical field, in, for example, the design of pipework in manufacturing plant, in oil delivery pipelines and in air conditioning and central heating systems.

The invention claimed is:

1. A method of configuring or reconfiguring branches in tubing comprising the step of configuring or reconfiguring the axes of at least two components of the branched structure to have a skew arrangement such that the axes are neither intersecting nor parallel, and in which at least one of the components of the branched structure itself has internal helical ridging and/or grooving adapted to reduce or eliminate turbulence and/or dead regions in flow through the tubing.

2. A method according to claim 1, in which the said internal helical ridging and/or grooving is adapted to cooperate with the skew arrangement.

3. A method according to claim 1, in which internal surfaces of the other of said components of the branched structure are configured or reconfigured to be smooth, with no sharp edges.

4. Tubing configured or reconfigured according to a method according to any one of claims 1 to 3.

5. Tubing according to claim 4, being blood flow tubing.

6. A method according to claim 2, in which internal surfaces of the other of said components of the branched structure are configured or reconfigured to be smooth, with no sharp edges.

7. Tubing configured or reconfigured according to a method according to claim 6.

8. Tubing according to claim 7, being blood flow tubing.

9. A method for configuring or reconfiguring branches in tubing having a branched structure including a main tube component joined to at least two branch tube components at a juncture for flow of fluid through said components, each of said components having a length and a flow axis extending centrally through a lumen of the component, comprising the step of configuring or reconfiguring said branch components to dispose said branch component axes in a skewed orientation at said juncture such that the axes are neither intersecting nor parallel and providing at least one of said components of said branched structure with an internal surface helical configuration arranged to reduce or eliminate turbulence and/or dead regions in fluid flow through said components.

10. A method according to claim 9, wherein said helical configuration is arranged to cooperate with fluid flow resulting from said skewed orientation of said axes.

11. A method according to claim 9, wherein the other of said components have internal surfaces configured or reconfigured to be smooth and free of sharp edges.

12. Tubing configured or reconfigured in accordance with the method of any one of claims 9, 10 or 11.

13. Tubing according to claim 12, wherein said fluid is blood.

* * * * *